(12) United States Patent
Chomas et al.

(10) Patent No.: US 7,534,210 B2
(45) Date of Patent: May 19, 2009

(54) METHODS FOR ADAPTIVELY VARYING GAIN DURING ULTRASOUND AGENT QUANTIFICATION

(75) Inventors: James E. Chomas, San Francisco, CA (US); Rickard C. Loftman, Menlo Park, CA (US); Constantine Simopoulos, Menlo Park, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 346 days.

(21) Appl. No.: 10/770,724

(22) Filed: Feb. 3, 2004

(65) Prior Publication Data

US 2005/0187476 A1 Aug. 25, 2005

(51) Int. Cl.
*A61B 8/00* (2006.01)

(52) U.S. Cl. .................. 600/458; 600/437; 73/627; 73/631

(58) Field of Classification Search .......... 600/437, 600/458; 73/596, 627, 631
See application file for complete search history.

(56) References Cited

U.S. PATENT DOCUMENTS

| | | | | |
|---|---|---|---|---|
| 5,469,849 A | * | 11/1995 | Sasaki et al. | 600/443 |
| 5,579,768 A | | 12/1996 | Klesenski | |
| 5,860,931 A | * | 1/1999 | Chandler | 600/458 |
| 6,080,107 A | * | 6/2000 | Poland | 600/458 |
| 6,258,033 B1 | * | 7/2001 | Grenon | 600/458 |
| 6,398,733 B1 | | 6/2002 | Simopoulos et al. | |
| 6,438,258 B1 | * | 8/2002 | Brock-Fisher et al. | 382/128 |
| 6,494,841 B1 | | 12/2002 | Thomas et al. | |
| 6,503,203 B1 | | 1/2003 | Rafter et al. | |
| 6,579,238 B1 | * | 6/2003 | Simopoulos et al. | 600/443 |
| 6,666,824 B2 | * | 12/2003 | Rust et al. | 600/443 |
| 6,679,844 B2 | * | 1/2004 | Loftman et al. | 600/443 |
| 6,682,482 B1 | | 1/2004 | Krishnan | |
| 6,942,618 B2 | | 9/2005 | Simopoulos | |
| 2003/0236459 A1 | | 12/2003 | Loftman et al. | |

* cited by examiner

*Primary Examiner*—Ruth S Smith
*Assistant Examiner*—Parikha S Mehta

(57) ABSTRACT

Methods are provided for automatic setting of parameters for contrast agent quantification. Various processes may improve quantification. For example, for consistency in contrast agent quantification, a gain or other setting of an ultrasound system is automatically determined in response to destruction of the contrast agent or at the initiation of the contrast agent quantification procedure. Automatic setting of an adaptive gain provides equalized image intensity for each repetition of a contrast agent quantification procedure based on a same triggering event, the destruction of contrast agent. By synchronizing the adaptive setting algorithms with contrast agent destruction, similar base line information is provided for each iteration of a contrast agent quantification procedure. As another example, the contrast agent gain setting treats acoustic signals representing tissue or other non-contrast agent structure as noise, mapping the tissue values to a substantially constant low value within the dynamic range. As yet another example, by segmenting out blood pools or other areas of contrast agent likely to have contrast agents even after destruction, the resulting gain is more likely sensitive to the detection of perfused contrast agents.

22 Claims, 3 Drawing Sheets

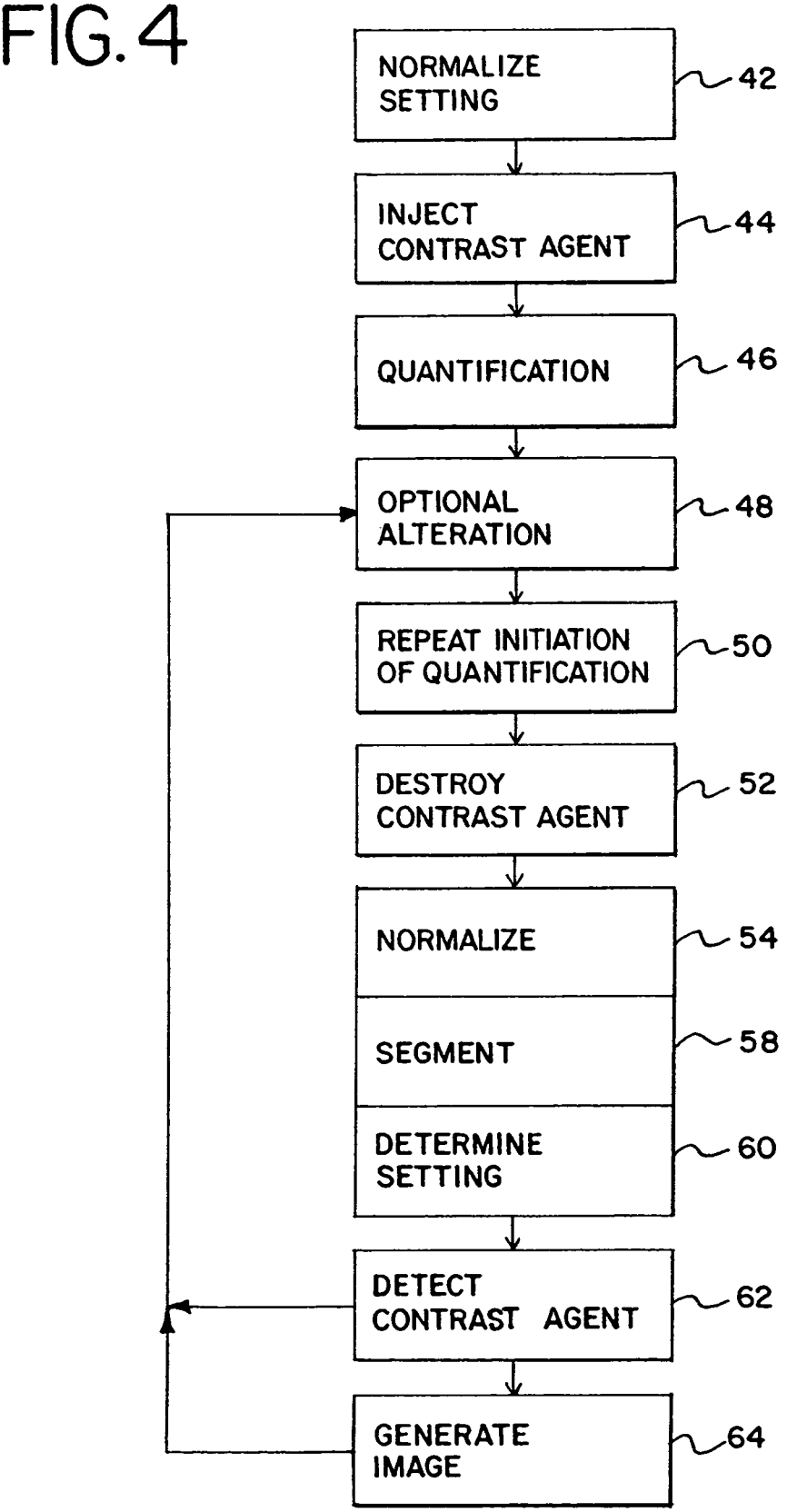

METHODS FOR ADAPTIVELY VARYING GAIN DURING ULTRASOUND AGENT QUANTIFICATION

BACKGROUND

The present invention relates to medical diagnostic ultrasonic imaging, and in particular to systems that adaptively set gain to improve such imaging.

In conventional ultrasonic imaging, a B-mode image signal is adjusted for gain before the signal is mapped to a range of gray levels or colors for display. The gain can conventionally be varied by the user using depth gain compensation (DGC) or a time gain compensation (TGC) control along with the master gain or B gain control. The DGC and TGC controls are conventionally variable in range only, and the master gain is independent of both range and azimuthal position. However, a lateral gain (LGC) may also be used.

Commercially available one-dimensional gain controls are often used by users to adjust brightness level. In many cases, users adjust the gain mainly to keep the regional mean of the soft tissue gray level within a narrow range of gray values. This preferred range is somewhat consistent from user to user, and in many cases users tend to adjust the gain to set the gray level for soft tissue to the 64th gray level on a linear map that maps 0 to black and 255 to white. However, gain adjustments for soft tissue brightness uniformity do not simultaneously optimize noise suppression and avoidance of saturation effects. Manual gain adjustments take time and require user expertise. Gain is frequently sub-optimal for some or all parts of an image. As a result, information can be lost by cutting off low-level signals or saturating high-level signals.

Various automatic gain setting algorithms have been used. One example is provided for color Doppler energy imaging. A measurement of the thermal noise along a center line is used to set the gain dependence on depth which can provide maximum signal sensitivity regardless of signals responsive to the transmission of acoustic energy. The user cannot adjust this gain, and the gain is not optimized as a function of multiple dimensions.

To more optimally control gain, U.S. Pat. No. 6,398,733 (assigned to the assignee of the present invention) discloses adaptively setting gain for a B-mode image. Spatial variance is used to identify regions of the image corresponding substantially to soft tissue. The system acquires a thermal noise frame with the transmitters turned off, and then uses the thermal noise frame and the identified regions of soft tissue both to locally and adaptively set the gain to cause soft tissue to be displayed at a constant average level throughout the image.

Optimal gain settings are different for imaging contrast agents. The target brightness may be manually adjusted for second harmonic B-mode contrast agent imaging. Gain optimization is important but difficult for imaging contrast agents. Contrast agent imaging may use low transmit powers, making setting the gain for adequate sensitivity difficult. Signals from tissue may be included in the contrast agent image, so the gain may reduce contrast between contrast agents and tissue.

Some contrast agent imaging protocols require brightness level comparison, requiring that the gain not be adjusted from before contrast agents are injected, or at least during the course of agent uptake into or outflow from tissue. Perfusion kinetics (e.g., arrival time, rise-time constant, peak enhancement or others) are quantified in some procedures. The procedures may be repeated during an imaging session by acoustic destruction of contrast agents, so any automatic gain setting is performed prior to the injection of contrast agents to provide consistency.

The various gain setting techniques discussed above for tissue imaging may be sub-optimal for other types of imaging, such as contrast agent imaging, and vice versa. Several different types of imaging are frequently used for imaging contrast agents, such as one image generated to represent contrast agents and another image generated to represent tissue. The contrast agent and tissue images are displayed separately or one overlaid on the other. The same gain curve may be applied for both images. Setting a gain curve based on the tissue image results in a poor gain curve for the contrast agent image. Gain setting algorithms adapted for identifying soft tissue may not be robust or optimal for the gain of the contrast agent image. The character of contrast agent images differs from tissue images. Since contrast agent imaging typically begins before introduction of contrast agent, any initial gain settings may be improper after administration of the contrast agent. Prior to the administration of contrast agent, automatic gain settings based on the contrast agent image may fail due to a lack of signal.

BRIEF SUMMARY

By way of introduction, the preferred embodiments described below include methods for automatic setting of parameters for contrast agent quantification. Various processes may improve quantification. For example, for consistency in contrast agent quantification, a gain or other setting of an ultrasound system is automatically determined in response to destruction of the contrast agent or at the initiation of the contrast agent quantification procedure. Automatic setting of an adaptive gain provides equalized image intensity for each repetition of a contrast agent quantification procedure based on a same triggering event, the destruction of contrast agent. By synchronizing the adaptive setting algorithms with contrast agent destruction, similar base line information is provided for each iteration of a contrast agent quantification procedure. As another example, the contrast agent gain setting treats acoustic signals representing tissue or other non-contrast agent structure as noise, mapping the tissue values to a substantially constant low value within the dynamic range. As yet another example, by segmenting out blood pools or other areas of contrast agent likely to have contrast agents even after destruction, the resulting gain is more likely sensitive to the detection of perfused contrast agents. Any one or a combination of multiple of the above-described processes may be used.

In a first aspect, a method for automatic setting in contrast agent quantification is provided. A contrast agent quantification procedure is initiated. During a same imaging session, the initiation of the procedure is repeated. A setting of an ultrasound system is automatically normalized as a function of received information each initiation.

In a second aspect, a method for automatic setting in contrast agent quantification is provided. Contrast agents are destroyed in a region of interest. A gain parameter is automatically set for the region of interest in response to the destruction of the contrast agent. Contrast agents are then detected in the region of interest after setting the gain parameter.

In a third aspect, a method for automatic setting in contrast agent quantification is provided. Contrast agents are injected into a region. Tissue values at a plurality of locations in the region are determined after the injection of contrast agent. A gain of an ultrasound system is adaptively varied based on the tissue values. The gain is associated with mapping the tissue values within an image to a substantially constant low value. An image of contrast agent responsive to the gain is then generated.

In a fourth aspect, a method for automatic gain setting in contrast agent quantification is provided. Acoustic energy is transmitted to destroy contrast agents. Data representing a region is acquired after the transmission of acoustic energy to destroy contrast agents. A gain of an ultrasound system is adaptively varied based on data representing a subregion of the region and free of data representing a different subregion associated with contrast agents.

The present invention is defined by the following claims, and nothing in this section should be taken as a limitation on those claims. Any of the various aspects, advantages, features, processes or methods described above may be used independently or in combination. Further aspects and advantages of the invention are discussed below in conjunction with the preferred embodiments and may be later claimed independent of the aspects noted above.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 4 is flow chart diagram of one embodiment of a method for automatic setting in contrast agent quantification.

DETAILED DESCRIPTION OF THE DRAWINGS AND PRESENTLY PREFERRED EMBODIMENTS

Figure 1:
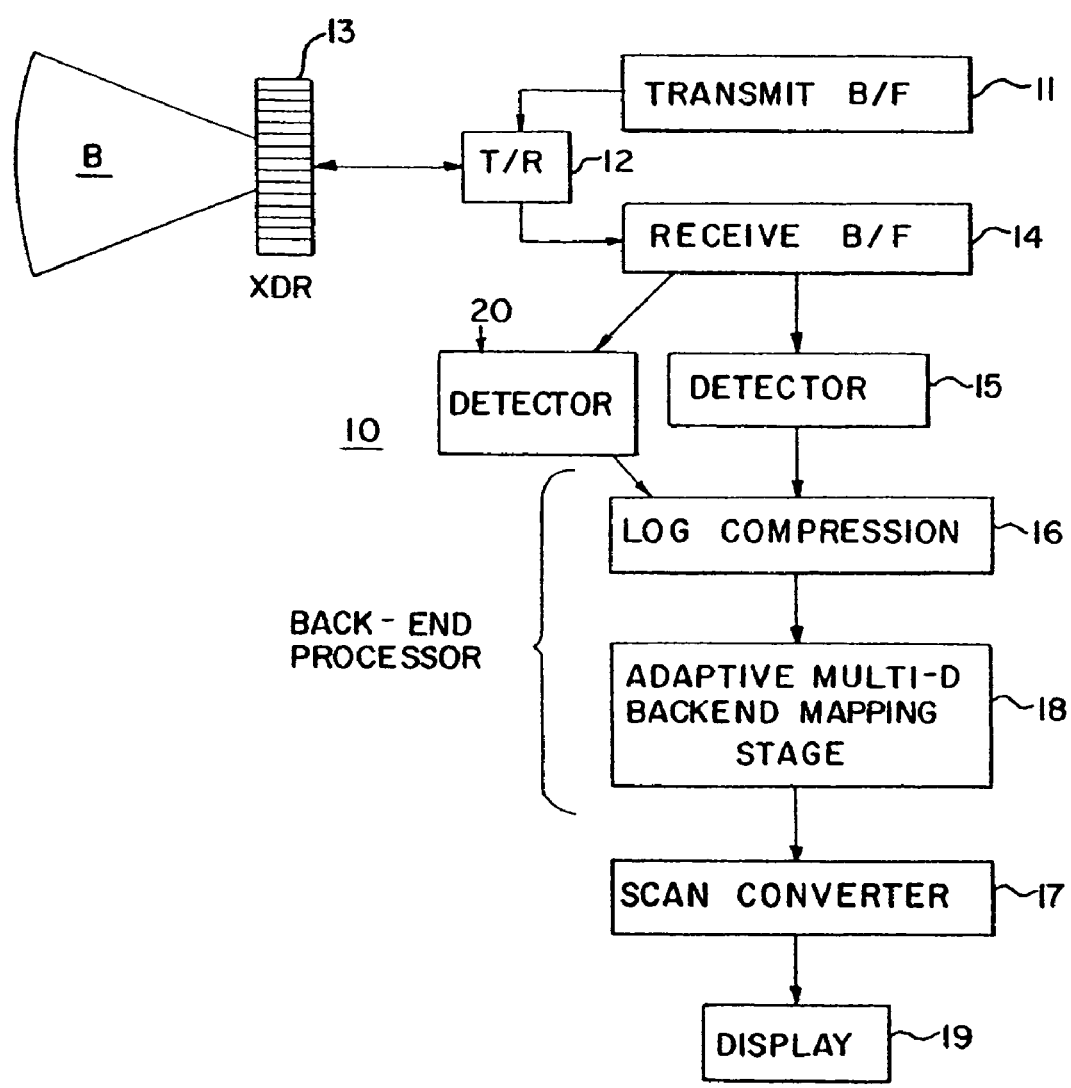
FIG. 1 is a block diagram of one embodiment of an imaging system with automatic setting for quantification.

FIG. 1 shows a block diagram of a medical diagnostic ultrasonic imaging system 10 for adaptively controlling a setting in a dual mode or contrast agent image. As shown in FIG. 1, a transmit beamformer 11 applies transmit waveforms via a transmit/receive switch 12 to a transducer array 13. The transducer array 13 produces ultrasonic pulses in response to the transmit waveforms, which pulses are directed into a field of view of a body B to be imaged. Returning echoes from the body B impinge upon the transducer array 13, which converts these echoes into receive signals that are transmitted via the transmit/switch 12 to a receive beamformer 14. The receive beamformer 14 applies appropriate delays and phase shifts to cause the receive signals from selected locations within the body B to add coherently.

These beamformed signals are applied to one or both of detectors 15, 20. The different detectors 15, 20 are used for different types of imaging. Different types of imaging use different transmit and associated receive sequences (e.g. single pulse versus multiple pulse), like transmit and different receive sequences (e.g. sharing at least one a transmit pulse for different receive combinations), different filters (e.g. removing fundamental versus harmonic information), different weights (e.g. no interpulse amplitude modulation versus interpulse amplitude modulation), different types of detection (e.g. intensity verses energy) and/or other imaging attribute.

In one embodiment, one detector 15 comprises a B-mode or amplitude detector. The detector 15 detects tissue information, but may also detect contrast agent, movement or other structure. The detector 15 detects fundamental frequency, second harmonic or other harmonic information responsive to a single transmission or multiple transmissions and associated receive signals.

The other detector 20 comprises an amplitude detector operating to determine contrast agent information using a method different from detector 15. For example, receive signals are combined and the result amplitude detected by a B-mode detector or a Doppler detector. The detector 20 detects contrast agent information. For example, any of the detectors and associated transmit and receive sequences disclosed in U.S. Pat. Nos. 6,494,841 and 6,682,482, the disclosures of which are incorporated herein by reference, are used. These detectors detect contrast agent information in response to different interpulse phase and/or amplitude modulation. Such detection methods may provide signals representing primarily contrast agent or contrast agent absent tissue information. In other embodiments, the detector 20 detects both contrast agents and tissue information, such as with single pulse or multi-pulse harmonic B-mode imaging. High power transmissions, low power transmissions or combinations of both may be used to avoid or cause destruction of contrast agent as part of imaging contrast agent. In one embodiment, contrast agent data is detected in response to multiple low power pulses with both interpulse amplitude and phase modulation.

The transmit and receive pulses for one detector 15 may be used for the other detector 20. For example, the detector 20 combines information responsive to three interpulse amplitude modulated transmit pulses with or without phase modulation. Echoes responsive to the one pulse are used by the detector 15 for B-mode tissue imaging. In other embodiments, additional, different or no pulses are shared by the two or more detectors 15, 20.

In alternative embodiments, only one detector 15, 20 is provided or used. The single detector 15, 20 sequentially detects data for two or more different types of imaging or only detects data for one type of imaging. For example, the detector 15, 20 detects both contrast agent and tissue information, such as detecting with a B-mode detector. As another example, only contrast agent information is detected.

The detected information is provided to a back-end processor that includes a log compression device 16 and an adaptive multi-dimensional back-end mapping stage 18. The mapping stage automatically determines and applies an overall gain and/or a gain curve optimized for the type of imaging. The output of the back-end processor is applied to a scan converter 17. The scan converter 17 generates display values upon a grid appropriate for a display 19.

All of the elements 11-17 and 19 can take any suitable form, and are not limited to any particular implementation. For example, the transmit and receive beamformers can be constructed as analog or digital devices, and any suitable transducer array can be used, including a single-element transducer array and phased arrays of various dimensions. Also, the system 10 may include additional elements in the signal path between the transducer array 13 and the display 19, and selected ones of the illustrated elements may be deleted or the order of some of the elements may be switched. For example, the order of the back-end processor and scan converter 17 can be altered. As another example, a filter or other element with programmable settings is provided in addition to or as an alternative to the log compression device 16 and the back-end mapping stage 18. A setting of the filter is automatically varied.

The system 10 responds to user input or a triggering event to automatically or adaptively set the gain or another setting (e.g., a filter bandwidth or response) for imaging. For example, the user presses a button to have the system 10 automatically set the gain. As another example, the system 10 automatically sets the gain in response to user selection of an imaging configuration, such as selecting a contrast agent imaging configuration. As yet another example, the gain setting is triggered in response to initiation of a quantification procedure or transmission of acoustic energy for destroying contrast agents. The user may further adjust the gain by controlling potentiometers or knobs for an average brightness, lateral brightness or depth brightness. Separate or shared controls may be provided for multiple types of imaging.

In the system 10, the adaptive multi-dimensional back-end mapping stage 18 controls the gain. The mapping stage 18 comprises one or more processors, filters, application specific integrated circuits, digital signal processors, analog components, digital components and combinations thereof. The mapping stage 18 can take many forms and in general automatically determines an overall, average or master gain as well as a lateral/depth gain curve. The mapping stage 18 sets and applies a brightness level for spatial locations within an image. In alternative embodiments, the mapping stage 18 alters the amplitude of data prior to log compression or after scan conversion.

In one embodiment, the mapping stage 18 includes hardware devices and/or software algorithms for determining gain parameters for two or more different types of imaging. The gain parameters comprise a lateral gain curve, a depth gain curve, an average or overall gain, a value or values used to determine gain information or other parameter representing gain for one or more spatial locations.

Figure 2:
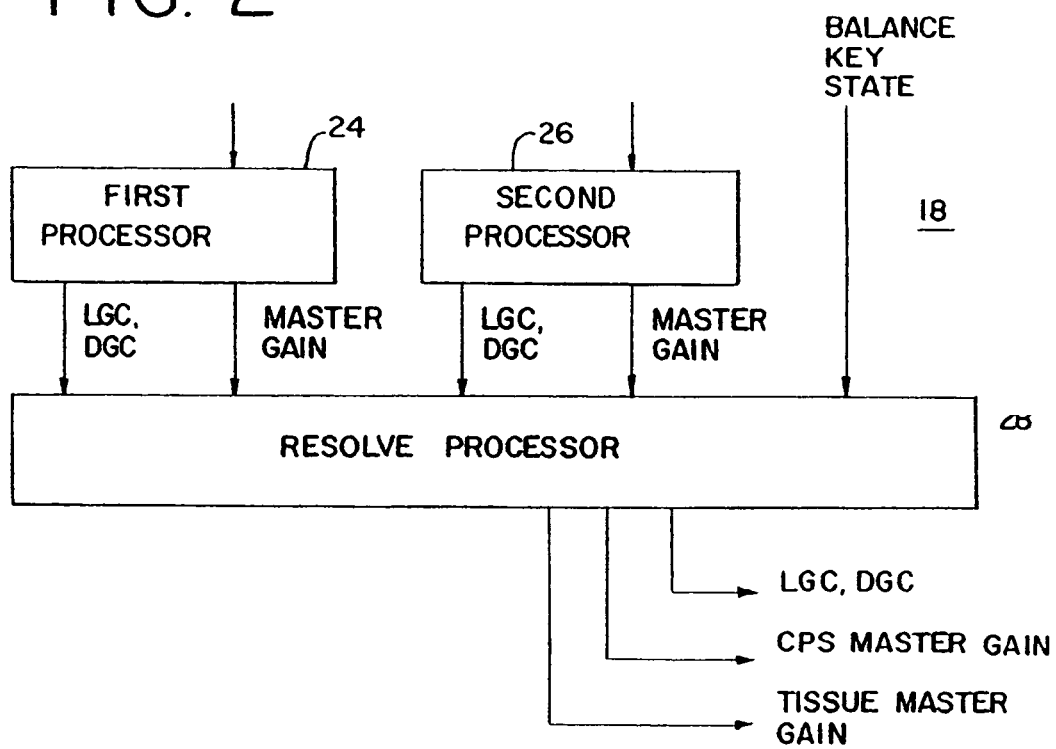
FIG. 2 is a block diagram of one embodiment of an automatic gain control system for multiple imaging modes.

FIG. 2 shows one embodiment of the mapping stage 18 for use with two different types of imaging. Two different processors 24 and 26 are implemented on the same or different hardware. One gain processor 24 determines gain parameters for a first type of imaging. The other gain processor 26 determines gain parameters for a second type of imaging. As shown, both two-dimensional or surface gain curves (LGC and DGC) and master or average gain are determined and output by both gain processors 24, 26. In alternative embodiments, different parameters are output or one gain processor 24 outputs a different type of parameter than the other gain processor 26.

A resolve processor 28 determines system or final gain information from the various gain parameters provided from the first and second gain processors 24, 26. The resolve processor 28 uses the same or different hardware as the first and second gain processors 24, 26. The resolve algorithm outputs both two-dimensional or surface gain curves (LGC and DGC) and a master or average gain for each of the two different types of imaging. In alternative embodiments, separate lateral and depth gain curves are output, only one gain parameter is output, only two gain parameters are output, a gain curve including spatially varying gain and the average gain, or other gain parameters are output.

In one embodiment, the two types of imaging used by the mapping stage 18 are contrast agent imaging and tissue imaging. Some contrast agent imaging techniques result in detected information representing contrast agents with minimal or almost no tissue information. The tissue image is displayed with the contrast agent image to provide reference tissue information prior to and during injection of contrast agents. The contrast agent image is overlaid on the tissue image, or the images are displayed separately. Different algorithms for determining gain allow automatic optimization of the gain algorithm based on the type of imaging. Gain algorithms are applied independently to data responsive to different types of imaging.

Figure 3:
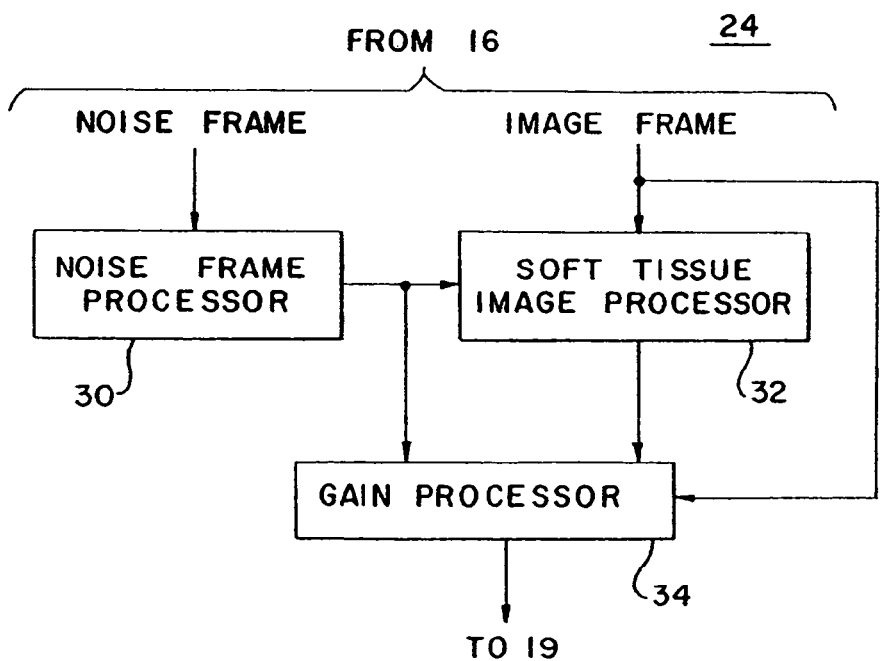
FIG. 3 is a block diagram of one embodiment of an automatic gain control system for a single imaging mode.

FIG. 3 shows one embodiment of implementation of the first processor 24 for use with tissue imaging. For example, the first processor 24 uses B-mode, second harmonic B-mode or other imaging techniques which provide tissue information alone or with other information. The embodiments described below in conjunction with FIG. 3 determine a local gain in both the near field and far field of the tissue image such that soft tissue is displayed at a substantially constant target value. Other embodiments disclosed in U.S. Pat. No. 6,398,733, the disclosure of which is incorporated herein by reference, or other embodiments for determining gain parameters for tissue information may be used.

As shown in FIG. 3, the first processor 24 includes a noise frame processor 30, a soft tissue processor 32, and a gain processor 34. The noise frame processor 30 generates an estimate of electronic or thermal noise as the noise varies over the frame. The soft tissue processor 32 generates a smoothed surface indicative of the intensity of soft tissue within an image frame at various locations in the frame. The gain processor 34 uses outputs from the processors 30 and 32 to adaptively adjust or determine either the average gain, depth gain and/or lateral gain. In one embodiment, one or more of the methods and systems of U.S. Pat. Nos. 5,579,768; 6,398,733 or 6,679,844, the disclosures of which are incorporated herein by reference, are used to determine one or more gain parameters for the tissue information.

The second processor 26 shown in FIG. 2 operates similarly to the first processor 24 as shown in FIGS. 2 and 3. Detected data responsive to a different type of imaging is input to the second processor 26. For example, the second processor 26 uses harmonic B-mode, loss-of-correlation, detection of non-linear fundamental, other multiple pulse detection techniques or other imaging techniques that primarily provide contrast agent information or provide contrast agent information with other information. A local gain in both the near field and far field of the contrast agent image is determined such that contrast agent is displayed at a substantially constant target value.

The second processor 26 is also implemented as shown in FIG. 3, except the soft tissue processor 32 is optional or not used. Rather than use the noise frame processor 30 based on thermal noise, any thermal noise as well as acoustic noise, such as data responsive to tissue, saturation, intact contrast agents and/or reverberations, is included. The noise frame processor 30 generates an estimate of acoustic noise as well as thermal noise as the noise varies over the frame in response to receive configuration associated with the contrast agent imaging. The acoustic and thermal noise signals are received in response to a transmission of acoustic energy with a similar intensity as used for contrast agent imaging. The gain processor 34 uses outputs from the processors 30 and 32 to adaptively adjust or determine the average gain, depth gain, lateral gain and/or other gain parameter. In one embodiment, one or more of the methods and systems of U.S. Pat. Nos. 5,579,768; 6,398,733 or 6,679,844 (U.S. application Ser. No. 10/176,274), the disclosures of which are incorporated herein by reference, are used to determine one or more gain parameters for the contrast agent information.

Other algorithms using the same or different inputs and processes may be used for adaptively determining one or more gain parameters for tissue, contrast agents or other information. In alternative embodiments, one mode of imaging is used that includes both tissue and contrast agent information, so a setting algorithm adapted for contrast agents is used. In other embodiments, other settings different from or in addition to gain (e.g., any of the gain parameters discussed herein) may be used, such as setting filter, detection, transmit beamforming, receive beamforming, scan conversion or triggering parameters.

FIG. 4 is a flow chart diagram of one embodiment of a method for automatic setting in contrast agent quantification. The acts shown in FIG. 4 may be provided in a different order, or fewer, different or additional acts may be provided. For example, acts 42, 46 and 48 may be skipped or otherwise not provided. As yet another example, the segmentation of act 58 is provided without the normalization and setting determinations of acts 54 and 60 or vice versa. As another example, a setting is automatically normalized in act 54 for contrast agent quantification without destruction of contrast agents in act 52. As yet another example, a setting of an ultrasound system is adaptively varied in act 60 to map tissue values to a substantially constant low value for generating a contrast agent image without the destruction of contrast agents in act 52. As yet another example, a setting is triggered in response to destruction of contrast agents without mapping tissue values to a substantially constant low value in act 60. The method shown in FIG. 4 is implemented using the system described above in FIGS. 1-3 or other systems now known or later developed.

In act 42, a setting is determined. For example, gain parameters or other settings are automatically determined or are set by the user. For automatic determination, any of the processes disclosed in U.S. Pat. Nos. 5,579,768, 6,398,733 or 6,679,844 or other now known or later developed processes are used. For example, a base line image, such as an image selected to identify tissue or an image selected to identify contrast agent is generated. A thermal noise image may alternatively or additionally be generated by receiving signals without generating a full strength acoustic signal. For example, the transmit path is configured for imaging without activating the waveform generator. Thermal noise generated by the transmit path electronics may cause some transmission of acoustic energy. The receive electronics in combination with any unintentional transmission of acoustic energy generates a thermal noise image. A gain and associated dynamic range is then automatically set in response to the baseline images. Normalization is provided by selecting settings based on a common configuration or information. For example, acquiring baseline images allows normalization of the settings regardless of the region being imaged. Different regions may be associated with different baseline images. By adaptively determining the setting, the setting is normalized to a given imaging region. Alternatively, a user attempts to adjust a setting to a normalized or common point, such as selecting a gain resulting in tissue values at a desired intensity level within the dynamic range.

For contrast agent quantification, the normalization of settings may provide more consistent results with other quantifications performed during the same or different imaging sessions. In medical diagnostic ultrasound, an imaging session typically takes between a quarter of an hour to an hour. A patient is continuously or periodically scanned with acoustic energy within the imaging session. Normalization of settings allows for comparison of the results. Greater normalization may result in differences or similarities between quantities having a greater medical significance.

In act 44, contrast agents are injected within a patient. In one embodiment, the contrast agents are injected through a catheter located adjacent or within a region of interest. Alternatively, the contrast agents are injected in one location of the body and travel to a region of interest, such as through the cardiovascular system. Any now known or later developed contrast agent may be used, such as microbubbles with or without coatings. Contrast agents respond differently to different acoustic intensities. Greater acoustic power or lower frequencies may result in a more likely destruction of contrast agent. Higher frequencies or lower power may avoid or minimize destruction of contrast agents. The injection of contrast agent is performed prior to beginning quantification or calculation, but may be performed after beginning quantification. Contrast agent quantification relies on the detection or change in detection of contrast agents.

In act 46, a contrast agent quantification procedure is performed. Any of various now known or later developed contrast agent quantification procedures may be used. For example, contrast agent quantifications assessing flow or perfusion are used. The wash-in of contrast agents is observed or measured, such as the perfusion of contrast agents within the myocardium, a tumor, liver or other tissue. Alternatively or additionally, wash-out procedures are performed where a perfused contrast agent is observed to leave a region of interest. As yet another alternative or addition, an absolute measurement of an amount of contrast agent within a region is performed. Any of various perfusion kinetics may be used, such as the time of arrival of contrast agents, the slope of a wash-in curve, the time to peak enhancement by contrast agents, the relative peak enhancement compared to surrounding regions, the time to wash-out or other now known or later developed contrast agent quantifications. The contrast agent quantification procedures are performed for cardiology, radiology, research, animal studies or other now known or later developed applications. As used herein, a contrast agent quantification procedure may rely on the calculation of a particular quantity, the measurement of a particular graph or slope, or the generation of images having observable features. By selecting normalized settings as part of the baseline acquisition before contrast agents are injected into the patient and maintaining the settings (e.g., fixed dynamic range and gain during the quantification procedure), the quantification is not biased by changes in the settings during the procedure.

In act 48, an optional alteration is performed. In one embodiment, the user alters the scan region, alters the viewing direction for a same or different scan region, or adjusts one or more imaging parameters, such as a type of detection. Other now known or later developed imaging parameters may be altered. Alternatively, quantification is to be repeated without alteration. Repetition of quantification allows for more thorough examination, more statistically accurate quantification, or analysis of additional information for diagnosis. Contrast agent quantification procedures are typically repeated for this additional information. The same or different quantification may be used for any repetition. For example, the same quantification procedure is performed for different regions of a myocardium.

In act 50, a contrast agent quantification procedure is initiated. In one embodiment, the initiation of the quantification is a repeat of the previous quantification of act 46. In other embodiments, a different quantification is performed in act 50, or the quantification of act 50 is the initial or first quantification procedure performed in an imaging session. The quantification procedure is initiated by user activation or triggering by the system as a function of time or a detected event. For example, the user depresses a button or provides other input initiating the quantification. The ultrasound system is either previously configured for performing the quantification or alters operation or imaging parameters to perform the quantification in response to the user input. For example, quantification related to contrast agent perfusion or wash-in of the myocardium or other structure is initiated by the user depressing a button. Wash-out or other quantification procedures may be initiated.

In response to the initiation or in response to a quantification process previously initiated, acoustic energy is transmitted to destroy contrast agents in act 52. For example, acoustic energy is transmitted having a high transmit power, low frequency, combinations thereof or other now known or later developed attribute adapted for destruction of contrast agent. The transmitted acoustic energy for destruction is transmitted as a fan beam or a plurality of beams transmitted along scan lines for destroying contrast agent in desired locations. The resulting destruction of contrast agents may leave some contrast agents even in the desired regions or may destroy all contrast agents. For example, in studying wash-in perfusion for the myocardium, the acoustic energy may destroy most of the contrast agents perfused within the myocardium, but only some of the contrast agents in the ventricle. Different amount of destruction may be provided, including lesser amounts of destruction. For example, a change in concentration of contrast agent is desired without necessary destruction of most or all of contrast agents in a region of interest.

The transmission of acoustic energy to destroy contrast agent is performed one or more times for any given quantification procedure. As any quantification procedures are repeated, the transmission of acoustic energy to destroy contrast agents is also repeated. After an initial wash-in of contrast agents due to previous quantification procedures or previous injection of contrast agent, the destruction of contrast agents is used to clear or destroy contrast agents for absorbing another wash-in or performing other quantification. The destruction resets the region of interest in preparation for further quantification. In alternative embodiments, the quantification is performed using a wash-out so that destruction of contrast agents is skipped and the agents are allowed to perfuse out of a region.

In act 54, one or more settings of an ultrasound system are normalized. The normalization occurs automatically for each repetition of the quantification or triggering event in a same quantification occurrence. For example, the normalization occurs automatically after destruction of contrast agents. The normalization is adapted to receive information from the region of interest after destruction. By automatically normalizing in response to received information, the setting adapts to the current imaging situation for improving image quality and consistency across multiple quantifications.

In one embodiment, settings are synchronized with the contrast agent quantification work flow. For each quantification, the baseline image acquisitions used for determining settings are acquired based on a common or more similar condition of the region of interest, the partial or complete destruction of contrast agents. Settings are equalized across quantifications to improve image quality and consistency. The baseline frames are automatically acquired as a function of when contrast agent destruction occurs. For example, baseline frames are acquired as a first image or acquisition after destruction, prior to substantial perfusion or within a time period. As a result, the user avoids manual adjustment of the setting, resulting in more reproducible quantification results. The number of acquisitions required during an imaging session may be reduced due to the automated work flow.

The synchronization of the normalization with destruction of contrast agent is performed using control signals in one embodiment. A control processor generates a control signal starting the normalization of the setting a certain time period after causing destruction of contrast agents. Alternatively, a feedback from the transmitter or transmit control processor is provided to a processor for normalization. In response to signals from the feedback, the normalization processor determines the setting.

Using gain as an example setting, a gain of an ultrasound system is adaptively determined as part of the normalization. The gain parameter for at least a region of interest is automatically set in response to the destruction of contrast agents, such as in response to the transmission of acoustic energy for destruction. The gain is then determined from received information after the destruction and substantially prior to detection of contrast agent, such as prior to the perfusion of a substantial number of contrast agents. As a result, the normalization is performed as a function of received information at the beginning of each repetition of the quantification or initiation of the quantification. The gain is calculated as a function of the data acoustically acquired substantially immediately after the destruction in one embodiment. The gain is separately determined for each performance of the contrast agent quantification procedure to provide consistency between quantification procedures within the imaging session.

The triggered normalization is performed for all possible settings, a subset of settings or a single setting. The settings are applied to one or more types of imaging. For example, contrast agent quantification procedures may include both tissue and contrast agent images detected separately. The normalized settings are applied to contrast agent image information, the tissue information or to both the contrast agent and tissue image information. Any now known or later developed adaptive determinations for a setting may be used. Alternatively, non-adaptive processes are used. In one example detailed below, one or more gain parameters are automatically and adaptively normalized. Gain and gain parameter are intended generally to indicate any one or more of a plurality of different gains, such as a depth gain, a lateral gain, an overall or system gain or dynamic range.

One embodiment for determining a gain setting acoustically acquires three image frames in response to or triggered after transmission of acoustic energy to destroy contrast agents. One frame is a thermal noise frame, acquired without generation of acoustic energy by a waveform generator. In alternative embodiments, the noise frame is previously acquired prior to the injection of contrast agents or for previous quantifications without reacquisition for every destruction frame. In this embodiment, the gain is calculated for both the tissue and contrast agent images or portions of an image, so a baseline tissue image and a baseline contrast agent image are acquired after destruction of contrast agents. A tissue image is acquired by configuring the system for generating tissue images as part of the quantification study. The contrast agent frame of data is acquired by configuring the system for detecting contrast agents. These baseline images may not have significant signals from contrast agents in the region of interest. For example, the myocardium may have no or few contrast agents. As a result, the contrast agent frame of data may indicate little or no contrast agent.

In optional act 58, one or more of the baseline images are segmented. By segmenting the image, spatial locations and data associated with one characteristic are differentiated from data in spatial locations associated with a different characteristic. For example, regions of the tissue or contrast agent baseline image associated with substantial amounts of contrast agent are segmented and not used in calculating gain. In a cardiology example, the ventricle may be associated with substantial amounts of contrast agent despite the transmission of destructive acoustic energy due to rapid in-flow of contrast agent, initial large concentration of contrast agents, focus of the destruction acoustic energy on the myocardium, or other reasons. By segmenting out areas associated with a substantial mass of contrast agents, the relative high echo intensity associated with contrast agent is prevented from altering the gain setting. Tissue, noise, perfused tissue or other types of signal may be segmented. As a result of the segmentation, a setting is adaptively varied based on one set of data representing one subregion of the region of interest and free of data representing a different subregion of the region of interest. In alternative embodiments, segmentation is not performed.

One embodiment for performing segmentation identifies signals in one of three categories based on different grey, intensity or echo levels, such as categories associated with noise (e.g., thermal noise or lack of signal due to dynamic range windowing), contrast agent and tissue (e.g., the myocardium in cardiology imaging). Contrast agents are likely the brightest signals within the frame of data, the myocardium is distinguished by lower signals, and the remaining information typically has regions associated with no signal or thermal noise of a level known from the thermal noise baseline frame of data or assumed by a low intensity level.

In one embodiment, the segmentation is performed using a tissue frame of data. The identified spatial locations are then used for setting the gain of the tissue and contrast agent frames of data. Alternatively, a contrast agent frame of data is used for segmentation. In yet other alternative embodiments, the tissue frame of data is used for segmentation to determine gain for the tissue frame of data, and the contrast agent frame of data is used for segmentation to determine the gain of the contrast agent frame of data.

In one embodiment, an iterative algorithm is used to identify spatial locations associated with desired or undesired signals. The grey level or intensity is mapped to a histogram. The histogram is then analyzed to associate levels associated with the three different types of regions. The pixels identified in the first iteration that belong to a particular region are then used to calculate a new value for the average gray level of that region. The standard deviation of the region is determined. Regions are identified by spatial locations with intensities or grey levels identified as close using a mean square calculation to an average grey level associated with that region. In one embodiment, a single iteration is performed, but multiple iterations may be used in other embodiments. Other algorithms for segmenting data may be used, such as thresholds or different functions now known or later developed.

The regions identified as part of the segmentation are then used for gain or other setting determination. For example, the region identified as tissue values, such as the myocardium, are used to set a two-dimensional gain (e.g., depth and lateral gains) to map the tissue values to a target grey level of zero or near zero across the contrast agent image. The thermal noise level or regions are mapped to a low target grey level which can be the same or different from the tissue grey level, such as a zero value for thermal noise and a different low value for tissue.

In act 60, a setting, such as the gain, is determined. The gain for the tissue frames of data is determined based on the tissue values or sub-regions of tissue in the tissue frame of data. In one embodiment, data identified by segmentation as associated with tissue is used. Alternatively, soft tissue regions are determined by statistics in the tissue and the signal-to-noise ratio. The tissue statistics are based on known speckle variance values, and a tissue signal-to-noise ratio is computed from the baseline tissue frame of data and the thermal noise frame of data. A speckle variance threshold and signal-to-noise ratio thresholds are then applied to the data within the tissue baseline frame of data. The thresholds are used to identify values with a speckle variance associated with tissue and a signal-to-noise ratio threshold indicating tissue rather than noise. The resulting pixel values are fit to a second order surface, low-pass filtered or otherwise used to estimate a gain curve. For a given spatial location, the gain is determined such that the intensity value is mapped to a target value or range of target values. A target value is selected to associate the tissue signals with a midrange of intensities or mid-to-low range of intensities, allowing highlighting of contrast agents mapped to higher intensity values from the contrast frames of data. As a result, the tissue regions of the baseline frame of tissue data and/or subsequent tissue frames of data are displayed around a target value and noise regions are displayed with a lesser gain to have a zero or substantially zero value. Other gain calculations may be used.

In one embodiment, a separate gain or gain curve for contrast frames of data is determined in act 60. The baseline frame of contrast agent data free of segmented data (e.g. contrast agent reflections from the ventricle) is used to determine the gain. Tissue values free of a separately acquired thermal noise frame of data are used for adaptively varying the gain. The contrast agent frame of data used as the baseline image is used for determining the gain without the thermal noise baseline image. The contrast agent frame of data includes both acoustic noise as well as thermal noise. The acoustic noise is associated with tissue values and other values responsive to transmitted acoustic energy generated through saturation, tissue leakage, intact contrast agents and other reverberations output from the contrast agent detection technique. The term acoustic noise is used since the signal is not generated by thermal noise and any resulting echoes from the transmission of acoustic energy after the destruction of contrast agents suggest that the signal and the baseline frame is a noise source or undesired information for imaging contrast agent. Setting gain using undesired acoustic noise allows equalization of intensities to eliminate back-end loss of tissue signals, reduction in electronic and acoustic noise and mapping of baseline tissue information or intensities to a target of value appropriate for contrast agent quantification. Maximum or increased sensitivity to contrast agent enhancement or perfusion is achieved when the tissue valves at the region of interest in the baseline contrast agent frame of data is mapped to a constant low-level grey scale value.

Since contrast agent quantification is based on time varying changes in the acoustic signal as the contrast agents perfused a region of interest, the desired gain causes the baseline image to appear with a uniform or a non-uniform but controlled target intensity range. The gain of the ultrasound system is adaptively varied based on the tissue values (acoustic noise in the contrast agent baseline data). The gain is associated with mapping the tissue values within the contrast agent image to a substantially constant low value. Where segmentation issued, the adaptive variation of the gain is free of contrast agent values. Values from undesired contrast agents may be used in the gain determination, but adaptive variation free of contrast agent values is substantially provided due to the destruction of contrast agents. In one embodiment, a quadratic surface is mapped to the baseline valves (i.e., tissue, any contrast agent not segmented out, and thermal noise values) of the baseline contrast agent frame of data.

The baseline values except the segmented values are mapped to the quadratic surface. The quadratic surface constrains the gain along the lateral or depth dimensions to a slow variation. Alternatively, low pass filtering or other processes are used. The resulting quadratic surface or values are used to determine the gain for each spatial location. The gain is set such that the value is mapped to a target intensity or one of multiple target intensities or ranges of intensity. For example in myocardium analysis, signals produced in the myocardium after contrast agent destruction are likely non-contrast agent signals to be suppressed by mapping such values to a low output in the dynamic range. Suppression in the baseline frame of data or subsequent frames of data allows generation of an image with minimal or no contribution from data other than contrast agents.

In one embodiment, the gain is set such that the tissue values of the contrast agent image are within a lower 15 percent of the dynamic range. For example, the tissue values are mapped to a zero or substantially zero value. In one embodiment, values associated with tissue are mapped to a higher intensity value than values associated with thermal noise. The noise is mapped to a zero value or a different value. In one embodiment, the noise is mapped to a non-zero but low value for user familiarity. The tissue values are mapped to the same values as a thermal noise or a higher value using either the contrast agent baseline image alone or with the thermal noise baseline image. As a result, the gain is set such that the tissue values are substantially at a bottom of the dynamic range for the contrast agent image. By allowing tissue values to be mapped higher than noise values, a tissue signal is viewable by the user but contributes little intensity. As a result, subsequently perfused contrast agents are seen to perfuse into tissue but with a much greater intensity than the tissue.

Resulting images are a combination of the tissue frame of data and contrast frames of data. For regions associated with the contrast agent frame of data, the gain is set as discussed above. The gain for the tissue regions is determined from the tissue gain discussed above. In alternative embodiments, a uniform gain curve for an entire image regardless of the source of data is determined.

The determined setting, such as the gain curve, is applied to the baseline frames of data and subsequent frames of data. For example, the settings are applied to all frames of data until a subsequent trigger event, such as a subsequent destruction of contrast agents. In other embodiments, the settings are applied to subsequent frames of data and not the baseline frames of data.

In act 62, contrast agents are detected in the region of interest after destruction during the contrast agent quantification procedure. The detection is as a function of the gain or other setting. For a contrast agent region, values similar to the baseline frame of data are mapped to a constant uniform low intensity and are unlikely to change. As contrast agent perfuses within the region of interest, the contrast agent is detected and displayed with an increased intensity as compared to other information. The increased intensity generates a higher grey level or higher signal level. As a result, the contrast agent is detected. The higher intensity of the contrast agent is mapped to other values within the dynamic range. The contrast agent information is then used for quantification.

In optional act 64, an image is generated. For example, at least one image of contrast agent responsive to the gain is generated for the contrast agent quantification procedures. A sequence of images is generated for each procedure in one embodiment. Each image includes spatial locations associated with a contrast agent, such spatial locations having contrast agent or expected to have contrast agent. For the myocardium example above, tissue regions associated with the myocardium are displayed in response to contrast agent detection techniques. Other portions of the images are displayed in response to tissue detection techniques. Different gains are applied for the different regions as a function of the type of data expected. Alternatively, separate images are generated using different detection techniques and are displayed separately or sequentially. Regions associated with the ventricle are displayed as tissue values, are masked out in the display, displayed as black or zero values, displayed as contrast agent values or subject to independent gain settings. Spatial locations segmented as discussed above are stored for quantification or other applications where segmentation may be useful, such as determination of separate gains using previously determined settings for segmented data.

In one embodiment, the initiation of quantification is repeated during the same image session. After detecting contrast agents sufficient for determining the quantity or desired information in act 62 and/or generating images in act 64, the process returns to either of acts 48 or 50. In returning to act 48, the same or different contrast agent quantification procedure is performed at least once for each of different views of a same region or for different imaging parameters. Alternatively, the process returns to act 50 and no further alterations are provided other than repeating the contrast agent quantification procedure. For example, the destruction of contrast agents, acquisition of data, automatic normalization or determination of a setting, detection of contrast agent and quantification are repeated in a sequence. A quantity is calculated as a function of each repetition of the detected contrast agent. By normalizing the setting or redetermining the setting after each destruction of contrast agent, any variations in imaging are accounted for in the setting, resulting in normalization. As a result, the same starting point is provided by a substantially uniform intensity across the region of interest after contrast agent destruction. In alternative embodiments, a contrast agent quantification procedure is performed only once. For example, a gain associated with contrast agent is determined by mapping both thermal noise and acoustic noise (e.g. tissue values) to a zero value, low value in the dynamic range, uniform value or range of values in the lower 15 percent, 10 percent, 5 percent or other value of the dynamic range.

In one embodiment, the normalization, such as the setting of the gain, is free of user input. The user activates initiation of the quantification, but is prevented from adjusting the setting as part of the quantification procedure. For example, user adjustment is prevented for a time period after the initiation of the quantification procedure or after normalization. By automatically invoking normalization after contrast agent destruction, workflow may be improved. For example, dynamic range and back-end gain changes are inhibited during wash-in, resulting in a wash-in curve determined from normalized information and not varied due to user adjustments during the procedure. In other embodiments, an offset control for an overall gain, for different gain parameters or for different gains applied to data for different detection technique, such as tissue offset in contrast offsets, are provided. The user is allowed a limited amount of control to adjust a gain during, before or after quantification procedures. For example, the user is allowed to adjust the gain from the normalized value such that certain signals are mapped to higher or lower intensities within the dynamic range. For example, the user adjusts the target value or target values. By limiting the adjustment, the effects on quantification are also limited. Alternatively, the offset control is provided without limitation. In one embodiment, an offset adjustment performed by the user is stored and used as an offset applied to the normalization setting of the subsequent quantification procedures without further user input. Alternatively, future automated settings are determined without reference to previous settings.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for automatic setting in contrast agent quantification, the method comprising:
    (a) initiating a contrast agent quantification procedure;
    (b) repeating (a) during a same imaging session; and
    (c) automatically normalizing a setting of an ultrasound system as a function of received information for each initiation of the contrast agent quantification procedure;
    wherein (c) comprises:
    (c1) determining tissue values at a plurality of locations in a region after injection of a contrast agent; and
    (c2) adaptively varying a gain of the ultrasound system based on the tissue values, the gain associated with mapping the tissue values within an image to a substantially constant low value; and
    further comprising:
    (d) generating at least one image of the contrast agent responsive to the gain for each initiation of the contrast agent quantification procedure.

2. The method of claim 1 further comprising:
    (e) injecting the contrast agent prior to (a);
    wherein (a) comprises initiating one of a wash-in and wash-out quantification procedure.

3. The method of claim 1 wherein (b) comprises performing the contrast agent quantification procedure at least once for each of at least one of: different views of a same region and different imaging parameters.

4. The method of claim 1 wherein (c) comprises normalizing as a function of the received information at a beginning of each repetition in (b).

5. The method of claim 1 further comprising:
    (e) transmitting acoustic energy to destroy the contrast agent in response to the initiations of the contrast agent quantification procedure in (a) and (b); and
    (f) detecting the contrast agent after (e);
    wherein (c) comprises determining the gain separately for each performance of the contrast agent quantification procedure, the gain determined from received information after (e) and substantially prior to (f).

6. The method of claim 1 wherein (c) comprises normalizing free of user input of the setting.

7. The method of claim 1 further comprising:
    (e) preventing user adjustment of the setting for a time period after each of the initiations of (a) and (b).

8. The method of claim 1 wherein (c2) is performed free of a separately acquired thermal noise frame of data.

9. The method of claim 1 wherein (c) comprises adaptively determining the gain from the group of: lateral gain, depth gain, system gain, dynamic range and combinations thereof of the ultrasound system from a baseline frame of data;
    further comprising:
    (e) applying the gain to the baseline frame of data and at least one subsequent frame of data.

10. A method for automatic setting in contrast agent quantification, the method comprising:
    (a) destroying a contrast agent in a region of interest;
    (b) automatically setting a gain parameter for receive signals from the region of interest in response to (a); and
    (c) detecting the contrast agent in the region of interest after (b);
    wherein (a) comprises transmitting acoustic energy; (b) comprises adaptively varying the gain of an ultrasound system based on tissue values, the gain associated with mapping the tissue values within an image to a substantially constant low value and (c) comprises detecting the contrast agent during a contrast agent quantification procedure.

11. The method of claim 10 wherein (b) comprises calculating the gain as a function of data acoustically acquired substantially immediately after (a).

12. The method of claim 11 further comprising:
    (d) applying the gain to the data acoustically acquired substantially immediately after (a) and subsequent data acquired during (c).

13. The method of claim 10 further comprising:
    (d) repeating (a), (b) and (c) in sequence;
    (e) quantifying as a function of each repetition of (c).

14. The method of claim 10 wherein (b) comprises:
    (b1) determining tissue values at a first plurality of locations in the region after (a);
    (b2) determining contrast agent values at a second plurality of locations in the region after (a), the second plurality of locations different than the first plurality of locations; and
    (b3) adaptively varying the gain of an ultrasound system free of the contrast agent values; and
    further comprising:
    (d) generating at least one image of the contrast agent responsive to the gain.

15. A method for automatic setting in contrast agent quantification, the method comprising:
    (a) injecting a contrast agent into a region;
    (b) determining tissue values at a plurality of locations in the region after (a);
    (c) adaptively varying a gain of an ultrasound system based on the tissue values, the gain associated with mapping the tissue values within an image to a substantially constant low value; and
    (d) generating an image of the contrast agent responsive to the gain.

16. The method of claim 15 wherein (c) is performed free of a separately acquired thermal noise frame of data.

17. The method of claim 15 wherein (c) comprises setting the gain such that tissue values are within a lower 15% of a dynamic range and contrast agent values are within an upper 85% of the dynamic range.

18. The method of claim 15 wherein (c) comprises setting the gain such that tissue values are substantially at a bottom of a dynamic range.

19. The method of claim 15 further comprising:
    (e) performing (b) after acoustic destruction of the contrast agent.

20. The method of claim 15 wherein (c) comprises setting the gain based on the tissue values and free of contrast agent values.

21. A method for automatic setting in contrast agent quantification, the method comprising:
    (a) transmitting acoustic energy to destroy a contrast agent;
    (b) acquiring first data representing a region after (a); and
    (c) adaptively varying a gain of an ultrasound system based on the first data representing a first sub-region of the region and free of the first data representing a second sub-region of the region, the second sub-region associated with the contrast agent;

wherein (c) comprises adaptively varying the gain such that tissue values are mapped to a substantially constant low value.

22. The method of claim 21 further comprising:
(d) detecting the contrast agent as a function of the gain;
(e) repeating (a), (b), (c) and (d) in sequence;
(f) quantifying as a function of each repetition of (d).

* * * * *